(12) United States Patent
Javey et al.

(10) Patent No.: US 10,330,637 B2
(45) Date of Patent: Jun. 25, 2019

(54) CHEMICALLY SENSITIVE FIELD EFFECT TRANSISTOR SENSORS

(71) Applicant: THE REGENTS OF THE UNIVERSITY OF CALIFORNIA, Oakland, CA (US)

(72) Inventors: Ali Javey, Lafayette, CA (US); Hiroshi Shiraki, Berkeley, CA (US); Hossain Fahad, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 176 days.

(21) Appl. No.: 15/366,353

(22) Filed: Dec. 1, 2016

(65) Prior Publication Data

US 2017/0146483 A1 May 25, 2017

Related U.S. Application Data (63) Continuation of application No. PCT/US2015/034068, filed on Jun. 3, 2015.
(Continued)

(51) Int. Cl.
*G01N 27/414* (2006.01)
*G01N 27/327* (2006.01)

(52) U.S. Cl.
CPC ..... *G01N 27/4141* (2013.01); *G01N 27/4148* (2013.01)

(58) Field of Classification Search
CPC ........... G01N 27/4141; G01N 27/4148; G01N 27/4143; G01N 27/4146; G01N 27/4145; G01N 27/414; G01N 27/3276
See application file for complete search history.

(56) References Cited

U.S. PATENT DOCUMENTS

| | | | |
|---|---|---|---|
| 2002/0132361 A1* | 9/2002 | Vossmeyer | B82Y 15/00 436/151 |
| 2004/0001778 A1* | 1/2004 | Chen | B82Y 10/00 422/88 |

(Continued)

FOREIGN PATENT DOCUMENTS

| | | |
|---|---|---|
| CN | 1473269 | 2/2004 |
| CN | 1997889 | 7/2007 |

(Continued)

OTHER PUBLICATIONS

Korean Intellectual Property Office (KIPO), International Search Report and Written Opinion, dated Sep. 24, 2015, related PCT international application No. PCT/US2015/034068, pp. 1-14, with claims searched, pp. 15-19. The relevance of non-English language KR 10-2103-0027199 is set forth therein.

(Continued)

*Primary Examiner* — Susan D Leong
(74) *Attorney, Agent, or Firm* — O'Banion & Ritchey LLP; John P. O'Banion (57) ABSTRACT

A system and method for chemical sensing of multiple gases or vapors with an array of chemical sensitive field effect transistor (CS-FET) devices that are highly sensitive, small in size and have low energy consumption. The sensor layer is an ultrathin film of transition metal oxide, rare earth metal oxide or metal nanoparticles that is formed between the source and drain electrodes on a silicon substrate. The work functions of the sensor layer can be manipulated by the adsorption of chemicals onto their surfaces. These changes cause a change in the surface potential of the underlying Si channel, leading to the current modulation of the devices. By selecting appropriate sensor layers, different chemicals will produce different output signals. External signal processing (Continued)

of these signals enables and sensor and array profile matching permits multi-gas detection.

15 Claims, 4 Drawing Sheets

Related U.S. Application Data (60) Provisional application No. 62/007,396, filed on Jun. 3, 2014.

(56) References Cited

U.S. PATENT DOCUMENTS

| | | | |
|---|---|---|---|
| 2004/0013571 | A1 | 1/2004 | Morris |
| 2004/0136866 | A1* | 7/2004 | Pontis ............... B82Y 10/00 422/400 |
| 2007/0181920 | A1* | 8/2007 | Renna ............... B81C 1/00047 257/288 |
| 2009/0256215 | A1* | 10/2009 | Novak ............... G01N 33/004 257/414 |
| 2010/0148222 | A1 | 6/2010 | Krauss |
| 2010/0282245 | A1 | 11/2010 | Star |
| 2010/0301398 | A1* | 12/2010 | Rothberg ............... G01N 27/27 257/253 |
| 2011/0089051 | A1 | 4/2011 | Wang et al. |
| 2012/0065948 | A1 | 3/2012 | Tan et al. |
| 2012/0168784 | A1 | 7/2012 | Fife et al. |
| 2013/0217598 | A1* | 8/2013 | Ludwig ............ G01N 33/54373 506/16 |
| 2013/0219988 | A1 | 8/2013 | Dutta |
| 2014/0329699 | A1* | 11/2014 | Esfandyarpour .. G01N 27/3278 506/6 |

FOREIGN PATENT DOCUMENTS

| | | |
|---|---|---|
| CN | 102192940 | 9/2011 |
| KR | 10-2013-0027199 A | 3/2013 |
| KR | 101275282 | 3/2013 |
| WO | 2008088780 | 7/2008 |

OTHER PUBLICATIONS

Tian, Lei et al., "3D differential phase-contrast microscopy with computational illumination using an LED array", Optics Letters, vol. 39, No. 5, Mar. 1, 2014, pp. 1326-1329.

Janata, Jiri et al., "Organic semiconductors in potentiometic gas sensors", J. Solid State Electrochem (2009) 13:41-49, published online Jun. 24, 2008.

Takulapalli, Bharath R. et al., "Electrical Detection of Amine Ligation to a Metalloporphyrin via a Hybrid SOI-MOSFET", J. Am. Chem. Soc. 2008, 130, 2226-2233, published online Jan. 29, 2008.

State Inellectual Property Office of the People's Republic of China (SIPO), official action dated Apr. 4, 2018, related Chinese patent application No. 201580022594.9, p. 1-7, claims examined, pp. 8-12.

* cited by examiner

CHEMICALLY SENSITIVE FIELD EFFECT TRANSISTOR SENSORS

CROSS-REFERENCE TO RELATED APPLICATIONS

This application is a 35 U.S.C. § 111(a) continuation of PCT international application number PCT/US2015/034068 filed on Jun. 3, 2015, incorporated herein by reference in its entirety, which claims priority to, and the benefit of, U.S. provisional patent application Ser. No. 62/007,396 filed on Jun. 3, 2014, incorporated herein by reference in its entirety. Priority is claimed to each of the foregoing applications.

The above-referenced PCT international application was published as PCT International Publication No. WO 2015/187878 on Dec. 10, 2015, which publication is incorporated herein by reference in its entirety.

STATEMENT REGARDING FEDERALLY SPONSORED RESEARCH OR DEVELOPMENT

Not Applicable.

INCORPORATION-BY-REFERENCE OF COMPUTER PROGRAM APPENDIX

Not Applicable

BACKGROUND

1. Technical Field

The present technology pertains generally to electronic gas sensors and more particularly to chemical sensitive field effect transistor (CS-FET) devices that can be used as low energy consumption, highly sensitive, small size, multi-gas detecting chemical sensors alone or in an array of sensors.

2. Background

Microelectronic chemical sensors have been explored as low-cost alternatives to gas chromatography and other complex and expensive laboratory sensing devices since the 1970's. One major class of chemical sensor technologies is based on a change in conductivity of a film of a chemically sensitive material such as a metal oxide or a polymer.

Most commercial gas sensors are based on thick ceramic films made of polycrystalline post transition metal oxide semiconductors such as $SnO_2$, ZnO and $In_2O_3$. The two types of metal oxide sensors are the n-type, which responds to oxidizing gases, and the p-type, which responds to reducing gases. For example, p-type sensors respond to oxidizing gases like $O_2$, $NO_2$, and $Cl_2$ as these gases remove electrons and produce holes, i.e. produce charge carriers. By comparison, the n-type sensor operates by reacting oxygen in the air with the surface of the sensor that traps any free electrons on the surface producing resistance in these areas. However, if the sensor is exposed to a reducing gas the resistance drops because the gas reacts with the oxygen and releases an electron.

The presence of gases exposed to the sensor is detected by monitoring the resistance of the oxide layer of the sensor. Incoming gas molecules react with pre-adsorbed oxygen, hydroxyl or water molecules resulting in an increase of the resistance for oxidizing gases such as $NO_2$ and $O_3$ and a decrease for reducing gases such as $H_2$, $H_2S$, $CH_4$, $NH_3$, CO and NO. The change of conductance is usually proportional to the concentration of the detected gas in the feed. The sensitivity is also dependent on the electronic properties of the oxide material as well as its porous microstructure.

The first reason that traditional oxide gas sensors require elevated operating temperatures is that the surface oxidation and reduction reactions that are necessary for both sensor response and recovery are too slow at temperatures below 200° C. Conventional metal oxide gas sensors reach higher selectivity by changing the chemical state of chemisorbed oxygen at the surface from $O_2^-$ to the more reactive $O^-$ by operating the sensor at temperatures typically between 300° C. and 600° C. At these elevated temperatures, certain feed gas molecules, such as hydrogen, methane, carbon monoxide, or hydrogen sulfide that can be chemically reduced by the oxygen species that are present at the surface of the metal oxide film.

The second reason for elevated operating temperatures is that adsorbed water on the metal oxide surface inhibits the sensor-analyte gas reactions, and therefore the water must be removed by operating at temperatures above 100° C., the boiling point of water. Desorption of adsorbed water molecules at high temperature therefore improves sensitivity further.

The consequence of these high temperature operational requirements is that the sensor must feature a heating unit to provide the required temperatures and therefore the power consumption of MOS based devices is very high compared to sensors fabricated from other materials. Power requirements also limit the portability of traditional MOS sensor systems.

Another important disadvantage of traditional oxide sensors is their lack of selectivity. Metal oxide-based gas sensors are often sensitive to more than one chemical species in a sample of feed gases and usually show cross-sensitivities. Consequently, the sensor measurements or signal from a target gas may be distorted or diminished by the interfering signal from the cross-reacting gases.

Accordingly, there is a need for gas sensing devices that can be operated at room temperature resulting in much lower power consumption and providing an ideal platform for portable devices. There is also a need for materials and methods that provide effective sensing at low cost. The present invention satisfies these needs as well as others and is generally an improvement over the art.

BRIEF SUMMARY

The present technology provides a single sensor or an array of chemically sensitive field effect transistor (CS-FET) devices that can be used as low energy consumption, highly sensitive, small size, multi-gas detecting chemical sensors. By way of example, and not of limitation, the devices have a base structure similar to a conventional Metal Oxide Semiconductor Field Effect Transistor (MOSFETs) except that a layer of sensor material such as a transition metal oxide (TMO) is used in place of the gate electrodes. The work functions of transition metal oxides (TMOs) deposited onto the channels of the CS-FET devices can be manipulated by the adsorption of chemicals onto their surfaces. These changes cause a change in the surface potential of the underlying Si channel, leading to the current modulation of the devices. By selecting the appropriate TMO or other sensor material, different chemicals will produce different output signals from the sensor. External signal processing of these signals will enable multi-gas detections. The CS-FET platform will be applicable for any kind of chemicals just by changing the choice of sensor material.

The technology also provides a system of an array of sensors with different sensitivities and selectivities. Each sensor is essentially a transducer that is capable of converting chemical interactions with an analyte gas stream into an electrical signal that may correspond to the identity and quantity of one or more of the constituent gases of the gas stream. Therefore, the identification of specific target gases may rely on not only the sensitivity and selectivity of one sensor but may also rely on analysis of the array response with pattern-recognition algorithms.

The chemical sensitive field effect transistor (CS-FET) sensors used individually or in an array generally comprise a source; a drain; and a sensor layer of a transition metal oxide (TMO) or other material disposed between the source and drain in place of a gate. The current modulation between the source and drain is induced by changes in work function and surface charges of the chemically sensitive TMO layer resulting from exposure to the gas.

In a preferred embodiment, the sensing profiles of the sensors of the array are collected and compared to a library of sensor profiles of single and combined gases to identify the constituent gases of an unknown stream of analyte gases. The profile library and comparisons can take place in the programming of a computer and display of the system.

In one embodiment, the CS-FET device is a unit in an array of CS-FET devices having different TMO layers sensitive to different gases. The array may also have redundancies in the type of sensors and the redundant sensor results may be confirmed and correlated.

It can be seen that the CS-FET sensors are fully CMOS compatible. Post-processing can be performed directly on to the same chip providing a platform for a fully integrated, scalable, compact lab-on-chip technology, which can be miniaturized and is compatible with existing mass production equipment. CS-FETs do not require short channel devices and are therefore compatible with technology nodes >90 nm. This advantage not only reduces fabrication costs but also reduces time-to-market for a full sensor system.

Silicon integrated circuit based fabrication processing can also be used to develop unique compact gas sensors that, unlike current sensors, will operate at room temperature, consume minimal power, exhibit superior sensitivity, provide chemical selectivity and multi-gas detection capabilities, and offer the prospect of very low cost replication for broad area deployment.

According to one aspect of the technology, a sensor apparatus is provided with a thin film, a nanowire bundle or a single nanowire sensitive element on a substrate.

Another aspect of the invention is to provide a sensor array and system for identifying and quantifying target gases from a feed or source of gases that has a library of sensor profiles and of array profiles of single gases and composite gases for comparison with acquired sensor profiles.

According to a further aspect of the technology, a method for identifying and quantifying target gases is provided that includes the creation of a library of sensor and array profiles for comparison with pattern recognition algorithms that allows on-line, real-time analysis that does not require significant sample preparation.

Further objects and aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawing which is for illustrative purposes only.

DETAILED DESCRIPTION

Referring more specifically to the drawings, for illustrative purposes, embodiments of the apparatus and methods for chemically sensitive field effect transistors and gas sensing using an array of sensors and a library of gas sensor profiles are generally shown. Several embodiments of the technology are described generally in FIG. 1 through FIG. 5 to illustrate the apparatus and methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
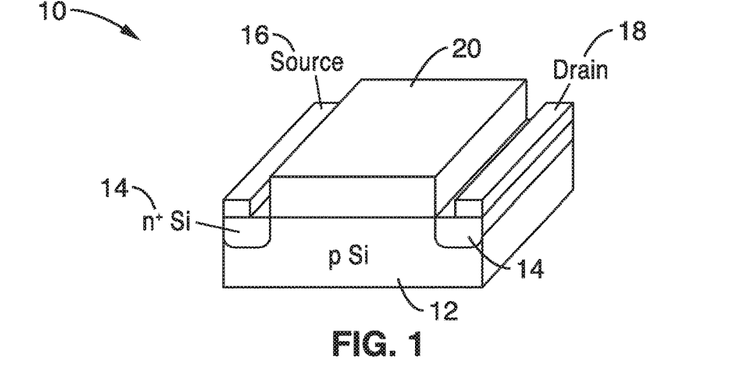
FIG. 1 is a schematic depiction of a sensor structure with a planar chemically sensitive thin film layer according to one embodiment of the technology.
Figure 2:
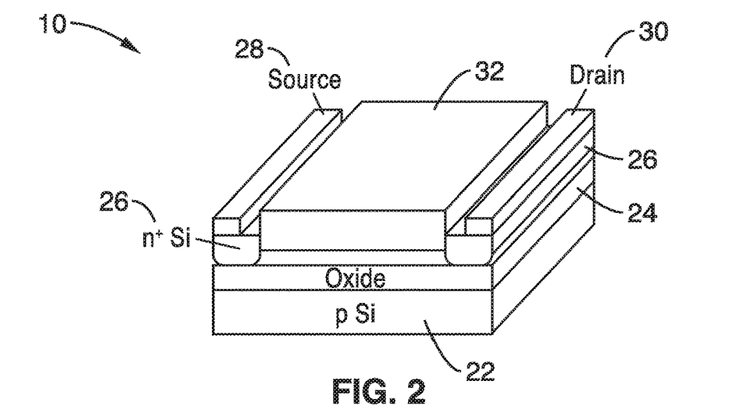
FIG. 2 is a schematic depiction of a sensor structure with a planar chemically sensitive thin film layer on a silicon on insulator base substrate according to an alternative embodiment of the technology.
Figure 3:
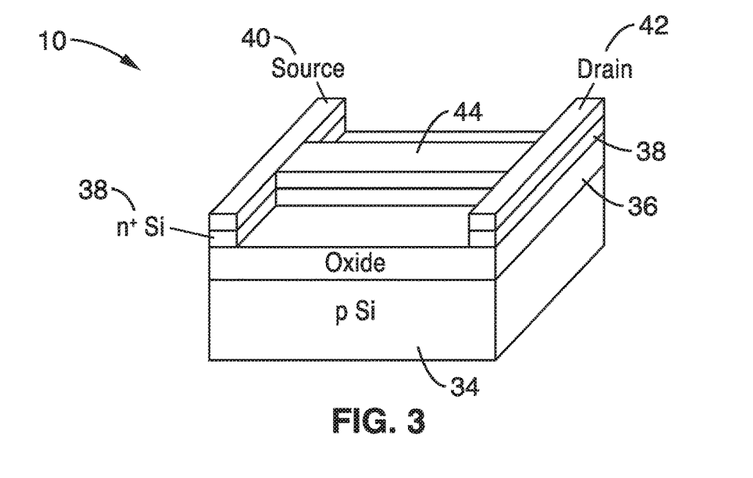
FIG. 3 is a schematic depiction of a sensor structure with a nanowire or nanowire bundle chemically sensitive layer on a silicon-on-insulator base substrate according to a second alternative embodiment of the technology.

Turning now to FIG. 1, one embodiment of an apparatus 10 for sensing target gases from a source stream or sample of gases is depicted schematically. Alternative embodiments of the sensor 10 are shown in FIG. 2 (2D: SOI) and in FIG. 3 (1D: nanowire). The individual sensor structures shown in FIG. 1, FIG. 2 and FIG. 3 are collectively referred to as "Chemical Sensitive FET" or "CS-FET" sensors.

The device illustrated in FIG. 1 is a 3D: planar version that resembles a conventional Si MOSFET structure without a gate structure. In this illustration the gate stack is replaced with ultrathin films of different transition metal oxides (TMOs) or metal nanoparticles.

The embodiment shown in FIG. 1 is built upon a p-type silicon base substrate 12. Although, a p-type substrate is illustrated here, it will be understood that the device could be built on an n-type substrate as well. Depletion regions 14 of n+Si form below the source electrode 16 and below the drain electrode 18. Subsequently, ultrathin films 20 of different TMOs or metal nanoparticles are deposited on the top surface of the Si layer 14 as illustrated in FIG. 1 rather than a gate stack.

TMOs are highly sensitive to ambient gases and their work function and surface charges are readily manipulated. The operational mechanism of the CS-FET is reminiscent of a conventional Si MOSFET, except that the measured current modulation between source and drain electrodes is not induced by applying a gate voltage but rather by changing the work function and surface charges of the ultrathin sensitive film layer 20 on top by the exposure of the layer to gases.

The ultrathin films 20 of TMO's or metal nanoparticles preferably range in thickness from approximately 2 nm to approximately 10 nm. In addition, the use of ultrathin oxide layers 20 renders them intrinsically sensitive to modifications at the surface. For example the work function of MoOx is known to exhibit extreme sensitivity to sub-monolayers of adsorbed gas molecules changing its work function from 6.6 eV for the clean MoOx surface to <5 eV for a covered surface. Ultrathin oxides further provide maximum gate coupling resulting in a strong drain current modulation in the channel of the MOSFET enabling high detection sensitivity. Furthermore, the deposition of ultrathin oxide films often leads to the formation of oxide nanoparticles which provide enhanced surface area for gas adsorption which further improves sensitivity.

Accordingly, the ultrathin films 20 that are selected should be sufficiently conductive to enable resistivity measurements. Good candidates for the chemically sensitive ultrathin layer 20 include a wide range of oxides for gas sensing. These include not only the post transition metal oxides, which also serve as transparent conductive electrodes in photovoltaic and display applications, but TMOs, whose typical resistivity is much higher.

Besides resistive semiconducting TMOs such as $TiO_2$, $V_2O_5$, $MoO_3$, $WO_3$, $Fe_2O_3$, NiO and their suboxides, the CS-FET configuration also enables the utilization of insulating TMOs such as $ZrO_2$, $HfO_2$, $Ta_2O_5$ and $Y_2O_3$ usually used as high-k gate dielectrics as well as rare earth metal oxides (RMOs) including $La_2O_3$, $Gd_2O_3$ and $Er_2O_3$ offering mixed valence as the active sensing medium.

In addition, chemically sensitive ultrathin layer 20 can also be composed of metal nanoparticles such as Au, Pd, Ag, Pt, Ru, and combinations of these materials, such as Au/Pd, Au/Ag, Au/Pt, Au/Ru that show high sensitivity to certain gases.

A list of potential metals whose oxides are candidates for integration into CS-FETs that can produce a characteristic fingerprint of the adsorbed gas on chemically sensitive ultrathin layer 20 include: Scandium (Sc), Titanium (Ti), Vanadium (V), Chromium (Cr), Manganese (Mn), Iron (Fe), Cobalt (Co), Nickel (Ni), Germanium (Ge), Gallium (Ga), Yttrium (Y), Zirconium (Zr), Niobium (Nb), Molybdenum (Mo), Technetium (Tc), Ruthenium (Ru), Rhodium (Rh), Palladium (Pd), Cadmium (Cd), Lanthanum (La), Hafnium (Hf), Tantalum (Ta), Tungsten (W), Iridium (Ir), Platinum (Pt), Gold (Au), Mercury (Hg), Thallium (Tl), Lead (Pb), Bismuth (Bi), Magnesium (Mg) and Aluminum (Al).

In addition, the sensitive ultrathin material layer 20 can also be a metal sulfide or an organic material that is reactive to target gases.

An alternative embodiment of a single sensor 10 is shown in FIG. 2. In this embodiment a p-type silicon substrate 22 is also used as a preferred base. An insulating layer 24 such as an oxide is disposed on top of the substrate base 22 and another p-type silicon layer 26 is placed on top of the insulating layer 24 to form a silicon-on-insulator (SOI) base structure. A source electrode 28 and a drain electrode 30 are placed on silicon layer 26 and depletion layers of n+Si form below the electrodes. A chemically sensitive ultrathin layer 32 is also placed on the surface of the top silicon layer 26 in this embodiment.

Suitable insulators that are used for insulating layer 24 are typically silicon dioxide or sapphire. The insulating layer 24 generally reduces parasitic device capacitance. Suitable materials for the chemically sensitive layer 32 are the same as with the chemically sensitive layer 20 in the embodiment that is described and shown in FIG. 1.

Another alternative embodiment of a single sensor device 10 is illustrated in FIG. 3. Here, the base layer 34 of p-type silicon has an optional insulating oxide layer 36 with a top silicon layer 38. Source electrode 40 and drain electrode 42 are disposed on the top surface of silicon layer 38.

The chemically sensitive element 44 can be either a single TMO or metal nanowire or a bundle or a network film of nanowires or other nanoparticles. The nanoparticles can be transition metal oxide nanoparticles or metal nanoparticles such as Au, Pd, Ag, Pt, Ru, and combinations of these materials, such as Au/Pd, Au/Ag, Au/Pt, Au/Ru and Pd/Ni metals.

An array of combinations of one or more types CS-FET gas sensors such as those described in relation to FIG. 1, FIG. 2 or FIG. 3 can be assembled. Sensors with different thin films of TMO's or other materials will demonstrate different gas selectivities. Gas adsorption modulates the current between source and drain of the underlying Si MOSFET in this embodiment. Processing the data generated from all of the individual sensors will allow the determination of a characteristic "fingerprint" or signal profile of the adsorbed gas which can be compared to a database of sensor profiles for gas identification.

Figures 4A, 4B:
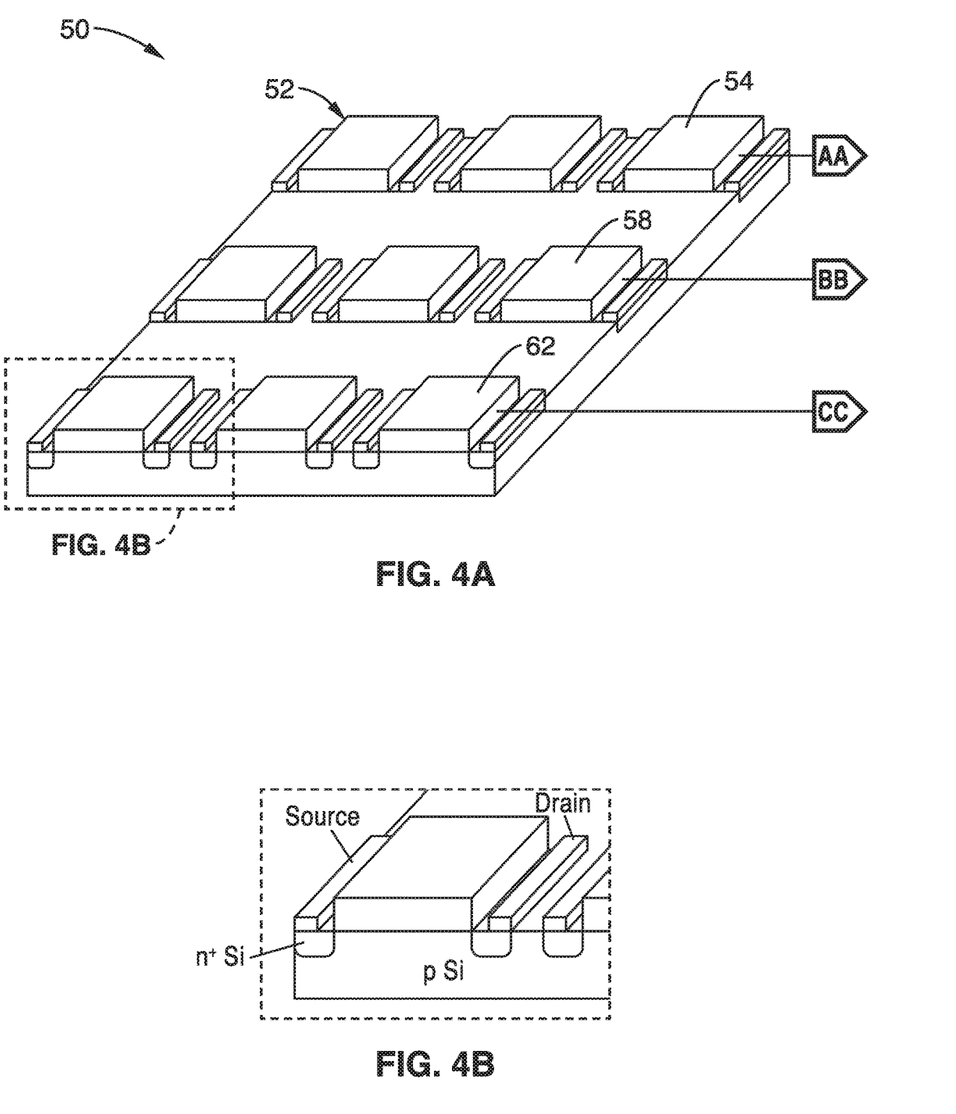
FIG. 4A through FIG. 4C is a system diagram of an array of the sensor structures of FIG. 1, sensor signal profiles and processor according to one embodiment of the technology.
Figure 4C:
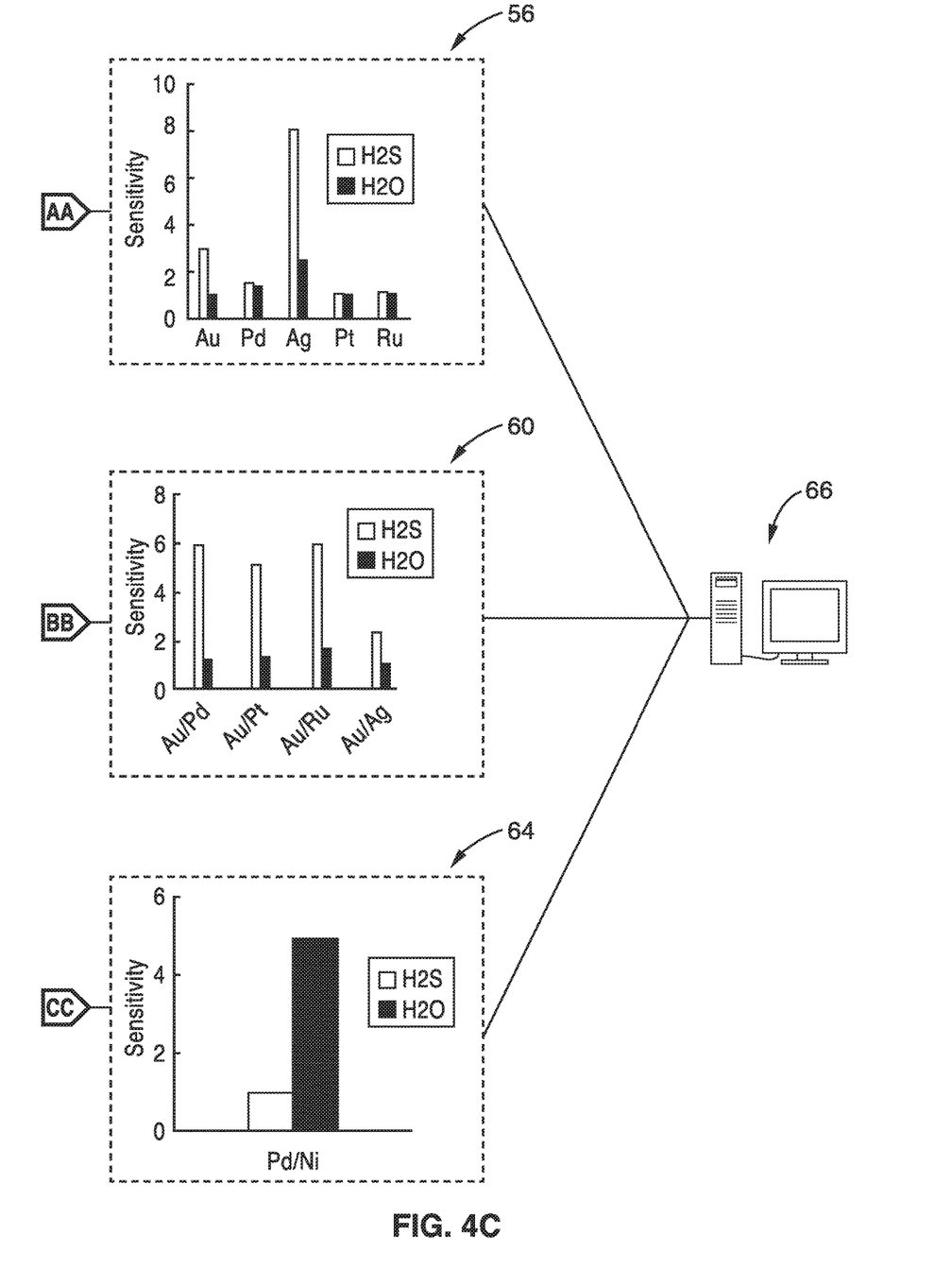

For example, a system 50 with an array 52 of nine different gas sensors and signal multiplexing electronics that are capable of recognizing individual or mixtures of analyte gases through pattern recognition is illustrated schematically in FIG. 4A through FIG. 4C. Each sensor 52, shown in detail in FIG. 4B will have a sensitivity to a particular gas depending on the chemically sensitive thin film that is used on the sensor. For example in FIG. 4C, sensor 54 shows a sensitivity profile 56 for a gas, which is $H_2S$ in this illustration. Likewise, sensor 58 of the array 52 has a different sensitivity signal profile 60 and sensor 62 has a different profile 64 for the same gas. The sensitivity profiles that are acquired from each of the sensors or the array 52 are processed by a computer 66 and compared to a library of known array sensor patterns and sensor sensitivity patterns to identify the constituent gases. The changes in the sensors due to gas adsorption or other interaction are preferably transduced into electrical signals, which may be pre-processed and conditioned before identification by the pattern recognition system of the programming of computer 66.

Figure 5:
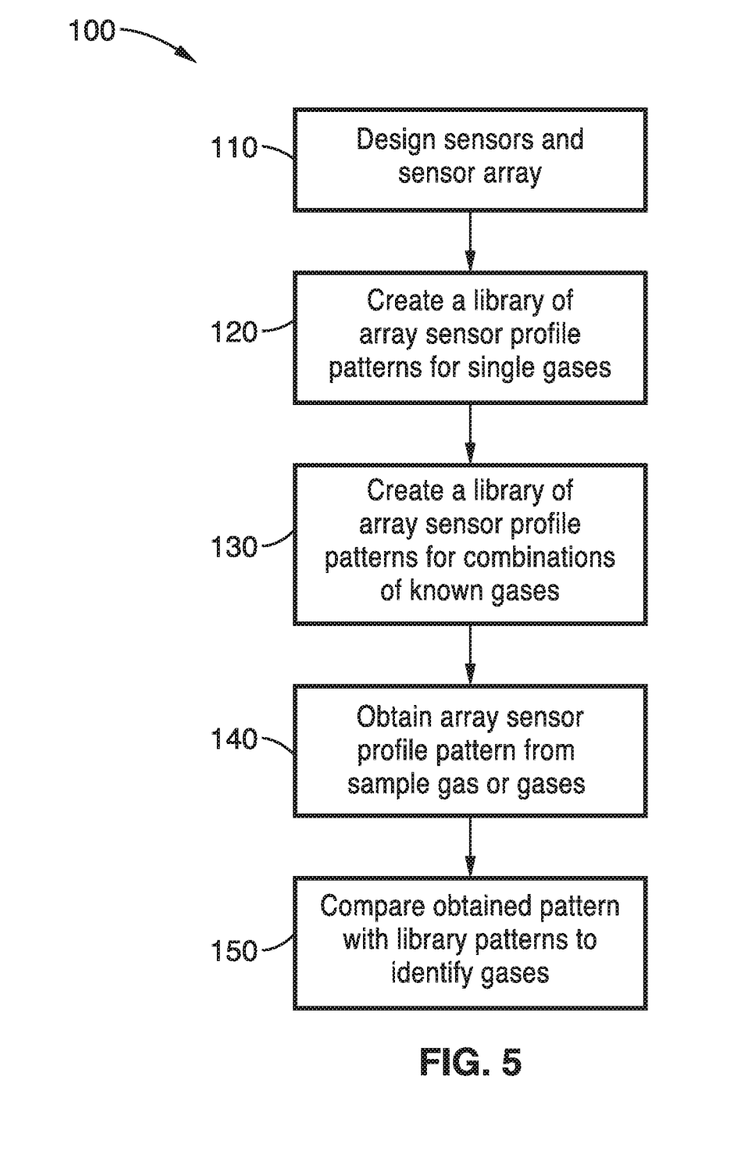
FIG. 5 is a schematic flow diagram of a method of gas analysis using an array of sensors and sensor response profile libraries according to one embodiment of the technology.

Referring now to FIG. 5, a method 100 for sensing gases with an array of sensors is described. The method 100 uses a distributed response of an array of multiple sensors to identify the unknown constituents of a gas sample.

At block 110 of FIG. 5, one or more arrays of sensors are designed and incorporated into the system. The sensors of the arrays are preferably connected to a recording and processing device in the system so that the sensor signals from each sensor of the array can be recorded and/or evaluated. The selection of sensors to be included in the array at block 110 can be influenced by the type of gas or mixture of gases that will be analyzed by the system. The array can also be assembled with a large number of sensors with a wide range of sensitivities to give the system a broad spectrum of detectable gases. The array can also be assembled with redundant sensors to produce redundant profiles that can be compared to verify the results and conclusions. If the profiles from the same type of sensor are substantially different then the results may be reevaluated.

Because individual sensors may or may not be selective for any particular gas, a distributed response of an array is used to identify the constituents of a gaseous sample. By using an array of different sensors, gases from a flow or sample can be distinguished and identified by a distinct "fingerprint" that each gas produces in the form of a pattern of measured electrical responses of the array.

The system is initially trained with the creation of libraries of array sensor profile patterns for a wide variety of single gases at block 120 of FIG. 5. The individual sensor profiles of each sensor type and array pattern are preferably recorded and placed into a searchable library of profiles for individual gases and groups of gases. Other parameters such as gas concentration, temperature and pressure may also be recorded at block 120.

Because it is often difficult for sensors to distinguish between two different gases, the system can also be trained with sensor and array data from combinations of gases at block 130. A searchable library of a wide variety of gas combinations at block 130 will give the system greater sensitivity and accuracy.

Once the libraries of array data have been assembled at blocks 120 and 130, the sensor array can be used to evaluate as sample of unknown gases at block 140. The array sensor data that is acquired at block 140 can be compared with the found in the libraries of array data for matching patterns at block 150.

The identification of target gases and gas concentrations can be conducted in-line and in real time.

From the discussion above it will be appreciated that the technology described herein can be embodied in various ways, including the following:

1. A chemical sensitive field effect transistor (CS-FET) apparatus, comprising: (a) a silicon substrate with a source electrode and a drain electrode; and (b) a sensing layer of an ultrathin film of chemically sensitive material on the substrate between the source and drain; (c) wherein current modulation between the source and drain is induced by changes in work function and surface charges of the sensing layer resulting from exposure to at least one gas.

2. The apparatus of any preceding embodiment, wherein the sensing layer comprises an ultrathin film of a transition metal oxide (TMO).

3. The apparatus of any preceding embodiment, wherein the transition metal oxide (TMO) of the sensing layer comprises a resistive semiconducting TMO selected from the group $TiO_2$, $V_2O_5$, $MoO_3$, $WO_3$, $Fe_2O_3$, NiO and their suboxides.

4. The apparatus of any preceding embodiment, wherein the transition metal oxide (TMO) of the sensing layer comprises an insulating TMO selected from the group $ZrO_2$, $HfO_2$, $Ta_2O_5$ and $Y_2O_3$.

5. The apparatus of any preceding embodiment, wherein the sensing layer comprises an ultrathin film of a rare earth metal oxide (RMO) selected from the group of oxides consisting of $La_2O_3$, $Gd_2O_3$ and $Er_2O_3$.

6. The apparatus of any preceding embodiment, wherein the sensing layer comprises an ultrathin film of metal nanoparticles selected from the group of metal nanoparticles consisting of Au, Pd, Ag, Pt, Ru, Au/Pd, Au/Ag, Au/Pt, Au/Ru and Pd/Ni metals.

7. The apparatus of any preceding embodiment, wherein the sensing layer comprises one or more nanowires selected from the group of nanowires consisting of transition metal oxide (TMO) nanowires, rare earth metal oxide (RMO) nanowires, and conductive organic polymer nanowires.

8. The apparatus of any preceding embodiment, wherein the silicon substrate further comprises: a top layer of p-silicon top coupled to the source electrode, drain electrode and sensing layer; a bottom p-silicon layer; and an insulator layer disposed between the top layer and the bottom layer.

9. The apparatus of any preceding embodiment, wherein the insulator layer of the substrate comprises an insulator selected from the group of silicon dioxide or sapphire.

10. A system for performing chemical sensing, the system comprising: (a) an array of CS-FET sensor devices, each CS-FET device comprising: (i) a silicon substrate with a source electrode and a drain electrode; and (ii) a sensing layer of an ultrathin film of chemically sensitive material on the substrate between the source and drain; (iii) wherein current modulation between the source and drain is induced by changes in work function and surface charges of the sensing layer resulting from exposure to at least one gas; (b) a computer processor operably coupled to the CS-FET array; and (c) a memory storing instructions executable on the computer processor, wherein when executed by the computer processor the instructions perform steps comprising: (i) acquiring sensor data from the CS-FET sensors of the array; (ii) comparing sensor data from the CS-FET sensors of the array with a library of array sensor data; and (iii) identifying a gas from the matching library sensor data.

11. The system of any preceding embodiment, wherein the sensing layer of each CS-FET device comprises a different ultrathin film of a transition metal oxide (TMO).

12. The system of any preceding embodiment, wherein the sensing layer of each CS-FET device comprises an ultrathin film of metal nanoparticles selected from the group of metal nanoparticles consisting of Au, Pd, Ag, Pt, Ru, Au/Pd, Au/Ag, Au/Pt, Au/Ru and Pd/Ni metals.

13. The system of any preceding embodiment, wherein the sensing layer of each CS-FET device comprises one or more nanowires selected from the group of nanowires consisting of transition metal oxide (TMO) nanowires, rare earth metal oxide (RMO) nanowires, and conductive organic polymer nanowires.

14. The system of any preceding embodiment, wherein the array of CS-FET devices comprise: (a) at least one CS-FET device with a sensing layer of an ultrathin film of a transition metal oxide (TMO); (b) at least one CS-FET device with a sensing layer of an ultrathin film of metal nanoparticles selected from the group of metal nanoparticles consisting of Au, Pd, Ag, Pt, Ru, Au/Pd, Au/Ag, Au/Pt, Au/Ru and Pd/Ni metals; and (c) at least one CS-FET device with a sensing layer of one or more nanowires selected from the group of nanowires consisting of transition metal oxide (TMO) nanowires, rare earth metal oxide (RMO) nanowires, and conductive organic polymer nanowires.

15. The system of any preceding embodiment, wherein the silicon substrate of each CS-FET device further comprises: a top layer of p-silicon top coupled to the source electrode, drain electrode and sensing layer; a bottom p-silicon layer; and an insulator layer disposed between the top layer and the bottom layer.

16. The system of any preceding embodiment, wherein the array comprises at least one duplicate CS-FET sensor device.

17. A method for chemical sensing of a gaseous sample, the method comprising: (a) creating a library of sensor profile patterns produced from exposure of a plurality of CS-FET sensors to one or more single gases; (b) acquiring sensor profile patterns from an array of CS-FET sensors exposed to a sample; and (c) matching the acquired sensor profile patterns to the library of sensor profile patterns to identify target gases in the sample.

18. The method of any preceding embodiment, further comprising: creating a library of sensor profile patterns produced from exposure of a plurality of CS-FET sensors to one or more combinations of known gases; and matching the acquired sensor profile pattern to the library of individual sensor profile patterns and array sensor profile patterns to identify target gases in the sample.

19. The method of any preceding embodiment, wherein the library of sensor profile patterns is produced from exposure of a plurality of CS-FET sensors to one or more single gases at a range of concentrations and temperatures.

20. The method of any preceding embodiment, wherein the library of array sensor profile patterns is produced from exposure of a plurality of CS-FET sensors to one or more single gases and combinations of gases at a range of concentrations and temperatures.

Embodiments of the present technology may be described with reference to flowchart illustrations of methods and systems, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A chemical sensitive field effect transistor (CS-FET) apparatus, comprising:
    (a) a silicon substrate comprising:
        (i) a source electrode;
        (ii) a drain electrode;
        (iii) a top layer of p-silicon tap coupled to said source electrode and said drain electrode;
        (iv) a bottom p-silicon layer; and
        (v) an insulator layer disposed between said top layer and said bottom layer; and
    (b) a sensing layer of an ultrathin film of chemically sensitive material coupled to said top layer of p-silicon of said substrate between the source and the drain electrodes;
    (c) wherein current modulation between the source and drain is induced by changes in work function and surface charges of the sensing layer resulting from exposure to at least one gas.

2. The apparatus as recited in claim 1, wherein the sensing layer comprises an ultrathin film of a transition metal oxide (TMO).

3. The apparatus as recited in claim 2, wherein said transition metal oxide (TMO) of said sensing layer comprises a resistive semiconducting TMO selected from the group $TiO_2$, $V_2O_5$, $MoO_3$, $WO_3$, $Fe_2O_3$, NiO and their suboxides.

4. The apparatus as recited in claim 2, wherein said transition metal oxide (TMO) of said sensing layer comprises an insulating TMO selected from the group $ZrO_2$, $HfO_2$, $Ta_2O_5$ and $Y_2O_3$.

5. The apparatus as recited in claim 1, wherein the sensing layer comprises an ultrathin film of a rare earth metal oxide (RMO) selected from the group of oxides consisting of $La_2O_3$, $Gd_2O_3$ and $Er_2O_3$.

6. The apparatus as recited in claim 1, wherein the sensing layer comprises an ultrathin film of metal nanoparticles selected from the group of metal nanoparticles consisting of Au, Pd, Ag, Pt, Ru, Au/Pd, Au/Ag, Au/Pt, Au/Ru and Pd/Ni metals.

7. The apparatus as recited in claim 1, wherein the sensing layer comprises one or more nanowires selected from the group of nanowires consisting of transition metal oxide (TMO) nanowires, rare earth metal oxide (RMO) nanowires, and conductive organic polymer nanowires.

8. The apparatus as recited in claim 1, wherein the insulator layer of said substrate comprises an insulator selected from the group of silicon dioxide or sapphire.

9. A system for performing chemical sensing, the system comprising:
   (a) an array of CS-FET sensor devices, each CS-FET device comprising:
      (i) a source electrode;
      (ii) a drain electrode;
      (iii) a top layer of p-silicon top coupled to said source electrode, drain electrode and a sensing layer of an ultrathin film of chemically sensitive material;
      (iv) a bottom p-silicon layer; and
      (v) an insulator layer disposed between said top layer and said bottom layer;
      (vi) wherein current modulation between the source and drain is induced by changes in work function and surface charges of the sensing layer resulting from exposure to at least one gas;
   (b) a computer processor operably coupled to the CS-FET array; and
   (c) a memory storing instructions executable on the computer processor, wherein when executed by the computer processor said instructions perform steps comprising:
      (i) acquiring sensor data from the CS-FET sensors of the array;
      (ii) comparing sensor data from the CS-FET sensors of the array with a library of array sensor data; and
      (iii) identifying a gas from the matching library sensor data.

10. The system as recited in claim 9, wherein the sensing layer of each CS-FET device comprises a different ultrathin film of a transition metal oxide (TMO).

11. The system as recited in claim 9, wherein the sensing layer of each CS-FET device comprises an ultrathin film of metal nanoparticles selected from the group of metal nanoparticles consisting of Au, Pd, Ag, Pt, Ru, Au/Pd, Au/Ag, Au/Pt, Au/Ru and Pd/Ni metals.

12. The system as recited in claim 9, wherein the sensing layer of each CS-FET device comprises one or more nanowires selected from the group of nanowires consisting of transition metal oxide (TMO) nanowires, rare earth metal oxide (RMO) nanowires, and conductive organic polymer nanowires.

13. The system as recited in claim 9, wherein the array of CS-FET devices comprise:
   (a) at least one CS-FET device with a sensing layer of an ultrathin film of a transition metal oxide (TMO);
   (b) at least one CS-FET device with a sensing layer of an ultrathin film of metal nanoparticles selected from the group of metal nanoparticles consisting of Au, Pd, Ag, Pt, Ru, Au/Pd, Au/Ag, Au/Pt, Au/Ru and Pd/Ni metals; and
   (c) at least one CS-FET device with a sensing layer of one or more nanowires selected from the group of nanowires consisting of transition metal oxide (TMO) nanowires, rare earth metal oxide (RMO) nanowires, and conductive organic polymer nanowires.

14. The system as recited in claim 9, wherein the array comprises at least one duplicate CS-FET sensor device.

15. The system as recited in claim 9, wherein
   wherein the insulator layer of said substrate comprises an insulator selected from the group of silicon dioxide or sapphire.

* * * * *